United States Patent [19]

Vogel

[11] Patent Number: 5,463,040
[45] Date of Patent: Oct. 31, 1995

[54] METHOD OF PREPARING ETOPOSIDE

[75] Inventor: Calvin Vogel, Netanya, Israel

[73] Assignee: Teva Pharmaceutical Industries, Ltd., Netanya, Israel

[21] Appl. No.: 266,923

[22] Filed: Jun. 28, 1994

[51] Int. Cl.$^6$ .......................... A61K 31/70; C07H 15/20; C07H 15/26
[52] U.S. Cl. .......................... 536/124; 536/4.1; 536/18.1; 536/18.5; 536/18.6
[58] Field of Search .................................. 536/18.1, 4.1, 536/18.5, 18.6, 124; 514/23, 54

[56] References Cited

U.S. PATENT DOCUMENTS

| | | | |
|---|---|---|---|
| 4,547,567 | 10/1985 | Umezawa et al. | 536/17.2 |
| 4,564,675 | 1/1986 | Kurabayashi et al. | 536/18.1 |
| 4,757,138 | 7/1988 | Fujii et al. | 536/18.1 |
| 4,900,814 | 2/1990 | Sterling et al. | 536/18.1 |
| 4,965,348 | 10/1990 | Saulnier et al. | 536/17.2 |
| 5,066,645 | 11/1991 | Oknuma et al. | 536/18.1 |
| 5,132,322 | 7/1992 | Lee et al. | 514/468 |
| 5,206,350 | 4/1993 | Wang et al. | 536/18.1 |

FOREIGN PATENT DOCUMENTS

| | | |
|---|---|---|
| 956939 | 10/1974 | Canada . |
| 26522 | 1/1977 | Israel . |
| 1205966 | 9/1970 | United Kingdom . |

OTHER PUBLICATIONS

*Clinical Pharmacy*, vol. 2, No. 2, Mar.–Apr. 1983, pp. 112–119 Phillips et al, "Review of etofoside".
*Helvetica Chemica Acta*, vol. 51, Fasciculus 1 (1968), pp. 163–168 Kuhn et al, "Abspatung von Acyl-Schutzgruppen be ialkaliempfindlichen Glucosiden,—Synthese von Podophyllotoxen–B–D–glucosid".
*Prog. Drug Res.*, vol. 33, (1989), pp. 169–266 Stahelin et al, "Frosm Podophyllotoxin glucoside to etoposide".

*Primary Examiner*—Ronald Griffin
*Attorney, Agent, or Firm*—Kenyon & Kenyon

[57] ABSTRACT

The present invention relates to a method of increasing the yield of etoposide produced relative to prior art processes. A residue obtained as a result of reacting etoposide triacetate with a first lower alkanol in the presence of a first transesterification catalyst is provided. This residue is then reacted with a second lower alkanol and a second transesterification catalyst.

37 Claims, No Drawings

METHOD OF PREPARING ETOPOSIDE

FIELD OF THE INVENTION

The present invention relates to an improved method for the preparation of etoposide.

BACKGROUND OF THE INVENTION

Glycoside derivatives of epipodophyllotoxin, for example, etoposide and teniposide, are valuable anti-neoplastic drugs. They have applications in the treatment of numerous cancers, including small-cell lung cancer and testicular cancer [*Clin. Pharmacy*, 2, 112 (1983)]. High efficacy and relatively low toxicity are other desirable characteristics of special interest in these drugs. Unless indicated otherwise, all references cited herein are incorporated by reference in their entirety.

The above materials are generally prepared using podophyllotoxin as a starting material. Podophyllotoxin is a component of extracts from the roots and rhizomes of the medicinal plants *Podophyllum emodi Wall* and *Podophyllum peltatum L*. Conversion of podophyllotoxin to etoposide or teniposide is a complicated process, involving many chemical steps and requiring several corrosive reagents. The use of these reagents presents not only handling and equipment problems but also causes environmental problems.

Disclosed processes for the conversion of podophyllotoxin to etoposide are based on the reaction of podophyllotoxin with gaseous hydrogen bromide. In the process described in Israeli Patent No. 26522, a suspension of podophyllotoxin in ethylene chloridediethyl ether is treated with a large excess of hydrogen bromide gas. The reaction intermediate product, 1-bromo-4'-demethylepipodophyllotoxin, is isolated by first vacuum distilling this highly corrosive solvent mixture and then precipitating the product from the resinous residue with acetone. The 1-bromo-4'-demethylepipodophyllotoxin is then hydrolyzed to give 4'-demethylepipodophyllotoxin. Reaction of 4'-demethylepipodophyllotoxin with the highly toxic benzyl chloroformate results in the formation of 4'-demethyl-4'-benzyloxycarbonyl epipodophyllotoxin (see, e.g., British Patent 1,205, 966). As described in Swiss Patent 514578 4'-demethyl-4'-benzyloxycarbonyl epipodophyllotoxin is condensed with 2,3-diacetyl-4,6-O-ethylidene-D-glucopyranose in the presence of boron trifluoride etherate to give the 2",3"-diacetyl-4' -benzoxycarbonyl derivative of etoposide. Finally, etoposide is obtained by removing the acetyl groups with methanol in the presence of zinc acetate and removing the carbobenzoxy group by catalytic hydrogenolysis.

This complicated process was simplified by the inventors of U.S. Pat. No. 4,900,814 by converting 1-bromo-4'-demethylepipodophyllotoxin to the corresponding 1-bromo-4'-demethyl-4'-acetylepipodophyllotoxin derivative, followed by hydrolysis to yield 4'-demethyl-4'acetylepipodophyllotoxin. Reaction with 2,3-diacetyl-4,6-O-ethylidene-1-tributylstannyloxy-D-gluco-pyranose gives, in a highly stereospecific reaction, etoposide triacetate from which etoposide may be obtained in a single transesterification reaction.

U.S. Pat. No. 4,900,814, discloses an example of a process for the preparation of etoposide which comprises the steps described in the following numbered paragraphs:

(1) Preparation of 4'-demethyl-4'-acetylepipodophyllotoxin by:
  (i) reacting podophyllotoxin with hydrogen bromide gas in methylene chloride-diethyl ester mixed solvent to yield 1-bromo-4'-demethylepipodophyllotoxin and
  (ii) reacting the 1-bromo-4'-demethylepipodophyllotoxin with an acetylating agent in the presence of an acid acceptor group, for example, pyridine, to yield 1-bromo-4'-demethyl-4'-acetylepipodophyllotoxin, which is then hydrolyzed to 4'-demethyl-4'-acetylepipodophyllotoxin;

(2) Preparation of beta-etoposide triacetate by condensing 4'-demethyl-4'-acetylepipodophyllotoxin with 4,6-ethylidene-2,3-diacetyl-1-tri(n-butyl)-stannyloxyglucopyranoside in the presence of a Lewis acid catalyst. The resulting product is a mixture of alpha- and beta-etoposide triacetate, which may be subjected to column chromatography to yield the substantially pure beta isomer, or this purification step may be left until later; and (3) Preparation of etoposide by solvolysis of the etoposide triacetate by reacting it with a lower alkanol in the presence of a transesterification catalyst. This yields a reaction mixture containing etoposide, along with a number of impurities. Pure etoposide is isolated through column chromatography, and the impurities are discarded.

SUMMARY OF THE INVENTION

A first advantage of the present invention is to provide an increase in the yield of etoposide relative to the yields achieved in conventional processes. This increase in yield is brought about by recycling a residue obtained after removing a first amount of etoposide, produced by reacting etoposide triacetate with a first lower alkanol in the presence of a first transesterification catalyst, from the reaction mixture and reacting the recycled residue with a second lower alkanol and a second transesterification catalyst. The recycled residue is preferably substantially free of etoposides. By "substantially free" is meant that the residue has been freed of etoposides to the extent commercially feasible. Generally, less than about 10%, preferably less than about 5% etoposides are present.

A further aspect of the invention relates to the treatment of etoposide triacetate to remove substantially all the alpha-etoposide triacetate and thus provides substantially pure beta-etoposide triacetate. Removing "substantially all" of the alpha-etoposide triacetate to yield "substantially pure" beta-etoposide triacetate means that the alpha-etoposide triacetate has been removed to the extent commericially feasible. In general, less than about 5%, preferably less than about 2% alpha-etoposide triacetate remains. The alpha-etoposide triacetate is preferably removed by refluxing a mixture of alpha- and beta-etoposide triacetate with methanol. This treatment is preferably included in the above process prior to the addition of the first lower alkanol/ transesterification catalyst.

These features provide significant advantages in the preparation of etoposide by increasing the overall yield of etoposide and simplifying the process steps.

As discussed above, etoposide triacetate, when reacted with a lower alkanol and a transesterification catalyst, yields etoposide as the major component of the resultant product mixture. A further aspect of the present invention relates to the isolation and characterization of one of the constituents present in this product mixture.

The constituent was isolated by column chromatography in a fairly pure state. Analysis by 300 MHz nuclear magnetic resonance (NMR) and mass spectroscopy identified this compound as an etoposide derivative in which the lactone ring is opened and converted to the corresponding alkyl ester. The compound has the structure as shown in formula I below:

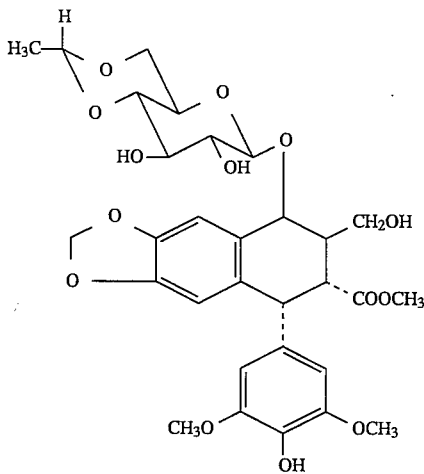

This compound, methyl 1-(4",6"-O,O-ethylidene-beta-D-glucopyranosyl)-4'-demethyl-epipodophyllinate (MEGDE), is herein purified and identified for the first time and forms a further aspect of the present invention. MEGDE is useful as an etoposide precursor.

It is clear that, depending on the lower alkanol used in the reaction with etoposide triacetate, the corresponding alkyl ester of the above compound will be obtained. Thus, the invention also relates to a process of preparing etoposide comprising the step of converting an alkyl 1-(4",6"-O,O-ethylidene-beta-D-glucopyranosyl)-4'-demethyl-epipodophyllinate to etoposide by reacting it with a lower alkanol in the presence of a transesterification catalyst.

These and other aspects and advantages of the invention and will become readily apparent to those skilled in the art, particularly after reading the detailed description of the preferred embodiments, examples, and claims to follow.

DETAILED DESCRIPTION OF THE PREFERRED EMBODIMENTS

According to a first embodiment of the invention a conventional process for the preparation of etoposide may be generally followed as described above until etoposide triacetate is obtained. Etoposide triacetate is then reacted with a first lower alkanol in the presence of a first transesterification catalyst for preferably from 40–100 hours, more preferably from 48–96 hours, and most preferably for 96 hours. The etoposide produced at this point is then isolated in a conventional manner. A second lower alkanol and a second transesterification catalyst are then added to the remaining residue and the reaction allowed to continue for from 40–100 hours, preferably from 48–96 hours, most preferably for about 48 hours. Additional etoposide can then be isolated from the resulting solution in a conventional manner, such as by removing the lower alcohol using, for example, vacuum distillation and by dissolving the residue, for example, in a mixture of methylene chloride and dilute aqueous acetic acid.

The etoposide triacetate used for the practice of the present invention is preferably beta-etoposide triacetate that is substantially free of alpha-etoposide triacetate. Such beta-etoposide triacetate may be obtained, for example, by purifying etoposide triacetate isomeric mixture using column chromatography. More preferably, the etoposide triacetate isomeric mixture is triturated (digested) in a lower alkanol, preferably methanol, at reflux, preferably for more than 1 hour and more preferably for about 2 hours to dissolve the alphae-topside triacetate. Once the alpha-etoposide triacetate is dissolved, it can be removed, for example, by filtration prior to the addition of the lower alkanol/transesterification catalyst to the resulting solid mixture.

Suitable first and second lower alkanols are $C_1$–$C_4$ alkanols. They are preferably selected from the group consisting of methanol, ethanol and propanol. More preferably, the first and second lower alkanols are identical and are both methanol.

Preferable transesterification catalysts are selected from the group consisting of anhydrous zinc acetate, zinc acetate dihydrate, zinc chloride and a mixed catalyst comprising zinc acetate dihydrate and zinc chloride. The first and second transesterification catalysts are preferably identical. They are more preferably both zinc acetate dihydrate.

The following examples are intended to exemplify the present invention and should not be construed as limiting the scope of the invention.

EXAMPLES

Example 1: Preparation of beta-etoposide triacetate

First, n-tributyl-stannyloxy-4,6-O,O-ethylidene-2,3-diacetyl glucopyranose is prepared in the following manner. A solution of 13.1 g (0.022 mole) of bis-(tributyltin)oxide in 25 ml dimethyl carbonate was flushed with nitrogen and then refluxed at 94° C. for two hours. To the resulting clear solution 13.3 g (0.04 mole) ethylidene glucose triacetate in 25 ml dimethyl carbonate was added, followed by refluxing for an additional two hours. The solvent was then removed on a flash evaporator to give the desired compound.

70 g of 4'-demethyl-4'acetylepipodophyllotoxin was then suspended in a solution of 195 g n-tributylstannyloxy-4,6-O,O-ethylidene-2,3-diacetyl glucopyranose in 500 ml methylene chloride and cooled while stirring to about 5° C. 62 ml boron trifluoride etherate was added at a rate such that the reaction temperature did not exceed 15° C. The temperature was then allowed to rise to 25° C. and the solution was stirred for 2 hours. The reaction solution was then poured into a solution of 84 g potassium hydrogen carbonate in 500 ml water, stirred for 5 minutes and the mixture filtered. The amorphous solid obtained was discarded and the filtrate allowed to separate. The upper layer was then discarded. The lower methylene chloride phase washed twice with water, dried over anhydrous sodium sulphate and after filtration all solvent was then removed by vacuum distillation. 161 g of an amorphous solid was obtained.

225 ml of methanol were added to this solid and refluxed for two hours with stirring. The reaction mixture was then cooled to about 0° C., filtered, and the solid washed with cold methanol and vacuum dried at 80° C. 51 g of beta etoposide triacetate essentially free of alpha etoposide triacetate was obtained whose assay was 91.3%.

Example 2: Etoposide from Beta-etoposide triacetate.

Beta-etoposide triacetate was first prepared using the procedure of Example 1. A mixture of 50 g beta-etoposide triacetate, 50 g zinc acetate dihydrate and 500 ml methanol were refluxed while being stirred for 96 hours. The mixture was cooled and the solvent removed by vacuum distillation. An amorphous solid residue remained. To this residue 300 ml methylene chloride, 300 ml water and 30 ml glacial acetic acid were added, and the mixture was stirred at ambient temperature (25° C.) until all the solid dissolved. The two phases now present were separated, and the upper aqueous phase was washed with methylene chloride. The combined methylene chloride phases were washed 5 times with 300 ml water. 50 ml of methanol was added to the first and third washes to prevent precipitation of etoposide. The methylene chloride solution was then dried over anhydrous sodium sulphate. After filtration and vacuum distillation, 39 g solid residue remained. HPLC analysis of this residue indicated that it consisted of 20% MEGDE, 66% etoposide, 5% picroetoposide and the remainder varying amounts of etoposide di- and mono-acetates. This solid residue was triturated twice with 300 ml methylene chloride. After each trituration the mixture was cooled and filtered. The solid remaining was etoposide. HPLC analysis showed it was 99% pure containing small trace amounts of the compound of formula I and etoposide acetates. The filtrates were pooled and solvents vacuum distilled to leave a solid mother liquor residue containing MEGDE which can then be further processed to yield a further amount of etoposide.

Example 3: Identification and Isolation of Methyl-1-(4'',6''-O,O-ethylidene-beta-D-glucopyranosyl)-4'-demethyl-epipodophyllinate Etoposide mother liquor residue was prepared as described in Example 2. A 5 g portion of this residue was taken and dissolved in 50 ml methylene chloride. This was subjected to column chromatography on a column containing 100 g slurry packed silica gel 60(63–200 micrometers) Merck 7734 in methylene chloride. The column was eluted with 1 liter of methylene chloride, followed by 1 liter of 1% methanol in methylene chloride, followed by about 3.25 liters of 3% methanol in methylene chloride, and fractions of 50 ml were collected. Fractions 52–54 contained trace amounts of etoposide acetates. Fractions 65–76 contained etoposide. Fractions 78–105 were pooled and the solvent evaporated. Analysis by HPLC System A (Novapak phenyl 3.9 mm×150 mm, acetonitrile 23%, sodium acetate buffer 77%, Flow 1.2 ml/min), 300 MHz NMR and mass spectroscopy identified this solid as 95% methyl-1-(4'',6''-O,O-ethylidene-beta-D-glucopyranosyl)-4'-demethyl-epipodophyllinate, 2.5% beta-etoposide and 2.5% picroetoposide/alpha-etoposide. Data from the NMR and mass spectroscopy analysis are presented below:

$^1$H-NMR (300 MHz,CDCl$_3$): 6.73 ppm(1H,s,H-8); 6.41(1H,H-5); 6.05(2H,s,H-2' and 6'); 5.92{2H,dd, OCH2O); 5.51(1H,s,OH); 5.04(1H,d,H-1); 4.73(1H,g.g-7); 4.59(1H,d,g-1); 4.40(1H,d,H-4); 4.20(1H,dd,g-6 eq); 3.88(2H,dd,H-11); 3.75(7H,s+m,2xOCH$_3$+g-3); 3.7-3.5(2H, g-6ax,g-2); 3.48(3H,s,C(O)OCH$_3$); 2.55(1H,m,H-2); 1.38(3H,d,g-8)

Mass Spectrum: m/z 638 (MH$^+$+NH$_3$)

Mol Wt: Calculated to be C$_{30}$H$_{36}$O$_{14}$=620

Example 4: Etoposide from Etoposide Mother Liquor Solids containing methyl-1-(4'',6''-O,-ethylidene-beta-D-glucopyranosyl)-4'-demethyl-epipodophyllinate 150 g zinc acetate dihydrate and 1500 ml methanol was added to 150 g of the etoposide, mother liquor residue solids prepared as described in Example 2. This mixture was stirred and refluxed for 48 hours. The mixture was allowed to cool and the solvent removed by vacuum distillation using a Rotavapor rotating evaporator. To the residue was added 600 ml methylene chloride, 75 ml glacial acetic acid and 500 ml water and the mixture stirred at room temperature for about half an hour to dissolve all the solids. The phases were then left to separate and the lower methylene chloride layer removed while the upper acidic aqueous phase was discarded. The methylene chloride solution was washed five times with 500 ml (each) water, 100 ml methanol was added to the first and third wash to prevent precipitation of etoposide. The methylene chloride portion was then dried over about 20 g anhydrous sodium sulfate. After filtration and vacuum distillation there remained 131 g solid. This solid was triturated for three hours with methylene chloride, The mixture was then cooled to 0° C., filtered and the filtered material dried. 51.6 g of solid was obtained. The trituration was repeated twice with 500 ml each methylene chloride to give 38 g etoposide.

I claim:

1. A method of preparing etoposide comprising:
providing a residue obtained by removing a first amount of etoposide from a reaction mixture produced by reacting etoposide triacetate with a first lower alkanol in the presence of a first transesterification catalyst; and
reacting said residue with a second lower alkanol and a second trans-esterification catalyst.

2. A method according to claim 1, wherein the etoposide triacetate is substantially free of alpha-etoposide triacetate.

3. The method according to claim 2, wherein the etoposide triacetate comprises less than about 5% alpha-etoposide triacetate.

4. The method according to claim 3, wherein the etoposide triacetate comprises less than about 2% alpha-etoposide triacetate.

5. A method according to claim 2, wherein the etoposide triacetate is triturated with a third lower alkanol prior to the addition of the first lower alkanol and the first transesterification catalyst.

6. A method according to claim 5, wherein the etoposide triacetate and the third lower alkanol are triturated for at least 1 hour.

7. A method according to claim 6, wherein the etoposide triacetate and the third lower alkanol are triturated for about 2 hours.

8. A method according to claim 6, wherein the third lower alkanol is methanol.

9. A method according to claim 1, wherein the etoposide triacetate is reacted with the first lower alkanol in the presence of the first transesterification catalyst for about 40 to 100 hours prior to removal of the first amount of etoposide.

10. A method according to claim 9, wherein the reaction time is about 96 hours.

11. A method according to claim 1, wherein the residue is reacted with the second lower alkanol and the second transesterification catalyst for about 40 to 100 hours.

12. A method according to claim 11, wherein the reaction time is about 48 hours.

13. A method according to claim 1, wherein the first and second lower alkanols are C$_1$–C$_4$ alkanols.

14. A method according to claim 13, wherein the first and second lower alkanols are selected from the group consisting of methanol and ethanol.

15. A method according to claim 13, wherein the first and second lower alkanols are identical.

16. A method according to claim 15, wherein the first and second lower alkanols are both methanol.

17. A method according to claim 1, wherein the first and second transesterification catalysts are selected from the group consisting of zinc acetate, zinc acetate dihydrate and a mixed catalyst comprising zinc acetate dihydrate and zinc chloride.

18. A method according to claim 17, wherein the first and second transesterification catalysts are identical.

19. A method according to claim 18, wherein the first and second transesterification catalysts are both zinc acetate dihydrate.

20. A method of preparing substantially pure beta-etoposide triacetate comprising triturating an isomeric etoposide triacetate mixture with a lower alkanol and removing the lower alkanol to isolate beta-etoposide triacetate.

21. A method according to claim 20, wherein the isomeric etoposide triacetate mixture and the lower alkanol are triturated for at least 1 hour.

22. A method according to claim 20, wherein the isomeric etoposide triacetate mixture and the lower alkanol are triturated for about 2 hours.

23. A method according to claim 21, wherein the lower alkanol is methanol.

24. The compound methyl-1-(4",6"-O,O-ethylidene-beta-D-glucopyranosyl)-4'-demethyl-epipodophyllinate as shown in the following formula:

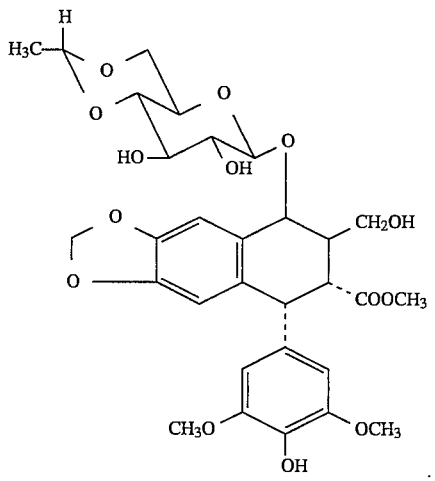

25. A method of preparing etoposide comprising the step of reacting a composition comprising alkyl-1-(4",6"-O,O-ethylidene-beta-D-glucopyranosyl)-4-demethyl-epipodophyllinate with a lower alkanol in the presence of a transesterification catalyst.

26. The method of claim 25 wherein said composition comprising alkyl-1-(4",6"-O,O-ethylidene-beta-D-glucopyranosyl)-4'-demethyl-epipodophyllinate is substantially free of etoposides.

27. The method of claim 26, wherein said composition comprising alkyl-1-(4",6"-O,O-ethylidene-beta-D-glucopyranosyl)-4'-demethyl-epipodophyllinate contains less than about 10% etoposides.

28. The method of claim 27, wherein said composition comprising alkyl-1-(4",6"-O,O-ethylidene-beta-D-glucopyranosyl)-4'-demethyl-epipodophyllinate contains less than about 5% etoposides.

29. A method according to claim 25, wherein the alkyl-1-(4",6"-O,O-ethylidene-beta-D-glucopyranosyl)-4'-demethyl-epipodophyllinate is reacted with the lower alkanol in the presence of transesterification catalyst for about 40–100 hours.

30. A method according to claim 29, wherein the reaction time is about 48 hours.

31. A method according to claim 25, wherein the alkyl-1-(4",6"-O,O-ethylidene-beta-D-glucopyranosyl)-4'-demethyl-epipodophyllinate is methyl-1-(4",6"-O,O-ethylidene-beta-D-glucopyranosyl)-4'-demethyl-epipodophyllinate and the lower alkanol is methanol.

32. A method according to claim 25, wherein the lower alkanol is a $C_1$–$C_4$ alkanol.

33. A method according to claim 32, wherein the lower alkanol is ethanol.

34. A method according to claim 32, wherein the lower alkanol is methanol.

35. A method according to claim 25, wherein the transesterification catalyst is selected from the group consisting of zinc acetate, zinc acetate dihydrate and a mixed catalyst comprising zinc acetate dihydrate and zinc chloride.

36. A method according to claim 35, wherein the transesterification catalyst is zinc acetate dihydrate.

37. A method according to claim 25, wherein the volume of the lower alkanol is at least ten times the volume of the transesterification catalyst.

* * * * *